United States Patent [19]

Ingmar

[11] Patent Number: 4,515,476
[45] Date of Patent: May 7, 1985

[54] DEVICE FOR THE OCULAR DETERMINATION OF ANY DISCREPANCY IN THE LUMINESCENCE CAPACITY OF THE SURFACE OF A TOOTH FOR THE PURPOSE OF IDENTIFYING ANY CARIED AREA ON THE SURFACE TO THE TOOTH

[76] Inventor: Bjelkhagen H. Ingmar, Hagagatan 54, 113 47 Stockholm, Sweden

[21] Appl. No.: 363,788

[22] Filed: Mar. 31, 1982

[30] Foreign Application Priority Data

Apr. 1, 1981 [SE] Sweden .................... 8102103

[51] Int. Cl.$^3$ .................... G01N 21/64; A61B 6/00
[52] U.S. Cl. .................... 356/318; 128/665; 250/458.1
[58] Field of Search .......... 356/317, 318, 417, 237; 350/96.26; 250/458.1, 459.1, 461.1, 461.2; 128/633, 634, 665

[56] References Cited

U.S. PATENT DOCUMENTS 3,494,354 2/1970 Yokota et al. .......... 350/96.26 X
4,290,433 9/1981 Alfano .................... 356/318

FOREIGN PATENT DOCUMENTS 1186602 4/1970 United Kingdom .......... 350/96.26

Primary Examiner—F. L. Evans
Attorney, Agent, or Firm—Burns, Doane, Swecker & Mathis

[57] ABSTRACT

A device for the ocular determination of any discrepancy in the luminescence capacity of the surface of a tooth (4) for the purpose of assessing the extent of any part (4a) of the surface of the tooth exhibiting caries and/or a coating and/or a defect. The surface of the tooth (4) is illuminated by a light (3) with a predetermined wavelength and/or wave range, for example a laser light. The luminescence capacity of the surface of the tooth at another wavelength and/or within another wave range shall be assessed, when any caried or similar part (4a) will show a discrepancy in relation to the normal luminescence capacity of the tooth (4) and will be perceived as a darker area. If the surface of the tooth (4) is illuminated by means of a light which is visible to the eye, then the observer (5) shall use an absorption filter (6) capable of absorbing light at the emitted wavelength or wave range reflected from the surface of the tooth. The invention may also be used in the course of treatment in order to determine when the caried part has been removed from the enamel surface and/or dentine surface produced by the treatment.

10 Claims, 4 Drawing Figures

DEVICE FOR THE OCULAR DETERMINATION OF ANY DISCREPANCY IN THE LUMINESCENCE CAPACITY OF THE SURFACE OF A TOOTH FOR THE PURPOSE OF IDENTIFYING ANY CARIED AREA ON THE SURFACE TO THE TOOTH

TECHNICAL FIELD

The present invention relates to a device for the ocular determination of any discrepancy in the luminescence capacity of the surface of a tooth, and the idea of invention is based more specifically on the fact or discovery that every area of the surface of a tooth exhibiting caries and/or a coating and/or a defect will have a luminescence capacity which differs from that of a sound tooth. The following specification deals only with caried areas.

The invention includes a device with which it has shown itself to be possible to make an instantaneous ocular determination of any discrepancy in the luminescence capacity of the surface of a tooth, with the intention of being able to create conditions under which the extent of an incipient and/or advanced caried area of the surface of a tooth may be assessed and of being able to determine what areas of the surface of a tooth are covered with a coating or are defective for some other reason. The following specification deals only with caried areas.

DESCRIPTION OF THE PRIOR ART

Previously disclosed are a number of different methods and procedures enabling the extent of a caried area on the surface of a tooth to be assessed, with the most common procedure involving the use of ordinary light to make an ocular examination of the surface of the tooth, thereby attempting to identify those areas on the surface of the tooth which exhibit a different reflectivity in relation to other sound areas. Incipient caries on an enamel surface will usually produce a reflection image which is rather lighter and rather more matt than that produced by the surface of a sound tooth.

Caries which has reached a more advanced stage will produce distinct markings on the enamel surface.

Probing may be used in order to determine the presence and extent of any caries.

Also previously disclosed is the principle of assessing the extent of caried areas on the surface of a tooth by the use of X-rays.

An article entitled "Human Teeth with and without Dental Caries studied by Visible Luminescent Spectroscopy" written by R. R. Alfano and S. S. Yao and published in the Journal of Dental Research, February 1981, describes laboratory equipment which makes use of laser light for the purpose of determining the presence of caried areas in a tooth.

DESCRIPTION OF THE PRESENT INVENTION

Technical Problem

It is a well-known fact that the method referred to above which utilizes the discrepancy in reflectivity is complicated, and the extent of the caried areas is especially difficult to assess by this method when the reflectivity between an area with incipient caries and the sound surface of the tooth is low in value.

The extent of caried areas in the fissure system on the occlusal surfaces is particularly difficult to assess by the reflection method.

The creation of conditions which will eliminate these problems represents a major technical problem.

The problem of locating those areas on the surface of the tooth with incipient caries has increased in significance of late, since it has been found that incipient caries is capable of healing itself if such conditions are treated at an early stage with fluorine or a similar substance.

Since the reflection method which is currently in use has been found to suffer from the inconvenience that it will permit the extent of the caried areas to be assessed only with difficulty and areas with initial caries to be located only in exceptional cases, the self-healing method referred to above has found a limited application.

Thus a major technical problem is associated with the creation of conditions and with the provision of equipment such that it will be possible effectively to assess the extent of that part of the surface of a sound tooth which exhibits incipient caries.

Although the publication referred to above indicates that laser light may be used to identify caried areas on the surface of a tooth, nevertheless it has proved to be difficult to design simple equipment based on this method which is easily used by the dentist.

Another problem which has been faced for a long time concerns the possibility of determining the extent of the caried area intermittently, although preferably continuously during a single treatment (by drilling away the caried area), at the same time avoiding the removal of an unnecessarily large part of the enamel surface and/or of the dentine.

Solution

The present invention proposes a solution to the problems referred to above involving the use of a device for the ocular determination of any discrepancy in the luminescence capacity of the surface of a tooth, thereby enabling the extent of a caried area on the surface of a tooth to be assessed. The surface of the tooth is illuminated by means of a light with a predetermined wavelength and/or a predetermined wave range. It has been found that the surface of the tooth will then be subject to luminescence and that it is possible to observe the luminescence capacity of the surface of the tooth at another wavelength and/or within another wave range other than that of the light used for the purpose of illumination. This observation will reveal a discrepancy between the luminescence emitted by the sound surface of a tooth and the luminescence emitted by a caried or similarly defective area.

If the light used for illumination is visible to the naked eye, then it will be necessary to filter the light emitted from the light source and reflected by the surface of the tooth and to filter any luminescence situated in the wavelength or within the wave range of the light used for illumination, thus enabling any discrepancy in the luminescence capacity to be assessed.

The invention is based, therefore, on the fact that the luminescence capacity at the surface of the tooth will vary considerably between a sound area on the surface of the tooth and an area of the surface of the tooth which has been attacked by caries.

The associated technical explanation may be assumed to be connected with the fact that a caried area has a crystalline structure which is different from that of the sound surface of a tooth, which means that the luminescence from the sound surface of a tooth will differ from the luminescence from a caried area.

The present invention proposes the possibility of causing the surface of the tooth to be illuminated by means of a laser light, for example an argon laser, in conjunction with which the observer, if the light is visible to the naked eye, will make use of an absorption filter capable of absorbing light at the wavelength emitted by the laser or at the wavelengths emitted by the laser. This means that only luminescent light from the tooth at wavelengths other than those emitted by the laser will be allowed to pass through the filter and to reach the observer, with differences in the luminescence capacity being used in order to reveal the presence of caried areas and parts.

The invention has also been found to be capable of extending to a device for the ocular determination of any discrepancy in the luminescence capacity of the surface of a tooth produced by the treatment (drilling) of a tooth enabling an assessment to be made during treatment of the extent of a caried area. This requires the surface of the tooth produced by the treatment to be illuminated in the course of the treatment either intermittently or continuously with a light with a predetermined wavelength and/or wave range. It has been found that the luminescence capacity of the surface of the tooth thus formed can be assessed at a wavelength or within a wave range other than that applicable to the light used for illumination, and that the resulting discrepancy between the luminescence capacity of the sound surface of a tooth and that of the caried surface of a tooth may be used in order to determine the extent of the caried area and the point at which the caried part has been removed completely.

The invention also proposes the use of a light-generating device of such a configuration as to produce a light with a narrow-band wavelength, for example a laser, and that an observer, in order to be able to determine by ocular means any discrepancy in the luminescence capacity if the light is visible to the naked eye, shall make use of an absorption filter. By causing the absorption filter to be capable only of absorbing light at a wavelength (or within a wave range) determined by the light-generating device, the absorption filter will eliminate any light reflected by the surface of the tooth (at the same wavelength as that of the light source) or any luminescent light generated within the wave range, although the filter will allow light at a different wavelength to pass through. This means that sound areas will appear to be brightly illuminated, whereas areas which have been attacked by caries will appear as dark areas.

The proposed device may also be used during treatment in order, at least intermittently, to be able to establish the extent of the caried area, thus permitting the treatment process to be monitored accurately.

Technical Advantages

The technical advantages which may be regarded as being associated with a device in accordance with the present invention are related principally to the fact that the caried areas on the surface of the tooth and/or the coating and/or any areas on the surface of the tooth which exhibit defects can be identified instantaneously and by ocular means considerably more easily by utilizing the luminescence capacity of the surface of the tooth than by assessing the extent of the caried areas on the basis of the reflectivity of the surface of the tooth.

Because the present invention offers the possibility of being able to assess the extent of the caried areas which are subject only to caries in its initial stages, it is also possible to treat these areas at an early stage with fluorine or a similar substance, thereby creating the conditions for self-healing to take place.

It has also been found that the invention offers the possibility of making a rapid and reliable assessment of the extent of those areas with incipient caries in the fissure system on the occlusal surfaces and on the adjacent surfaces.

It is also possible to examine the teeth by the proposed method and device without the need for special measures such as blacking-out or similar operations; the examination can take place under ordinary indoor lighting conditions.

Finally, the invention has been found to offer the advantage that it may be used at least intermittently during treatment, i.e. when drilling out the caried area, thus enabling the extent of the caried area to be determined and avoiding the need to remove an unnecessarily large part of the enamel and/or dentine.

BRIEF DESCRIPTION OF THE DRAWINGS

A preferred embodiment exhibiting the significant characteristics of the present invention is described in greater detail below in relation to the attached drawing, in which.

DESCRIPTION OF THE PREFERRED EMBODIMENT

Figure 1:
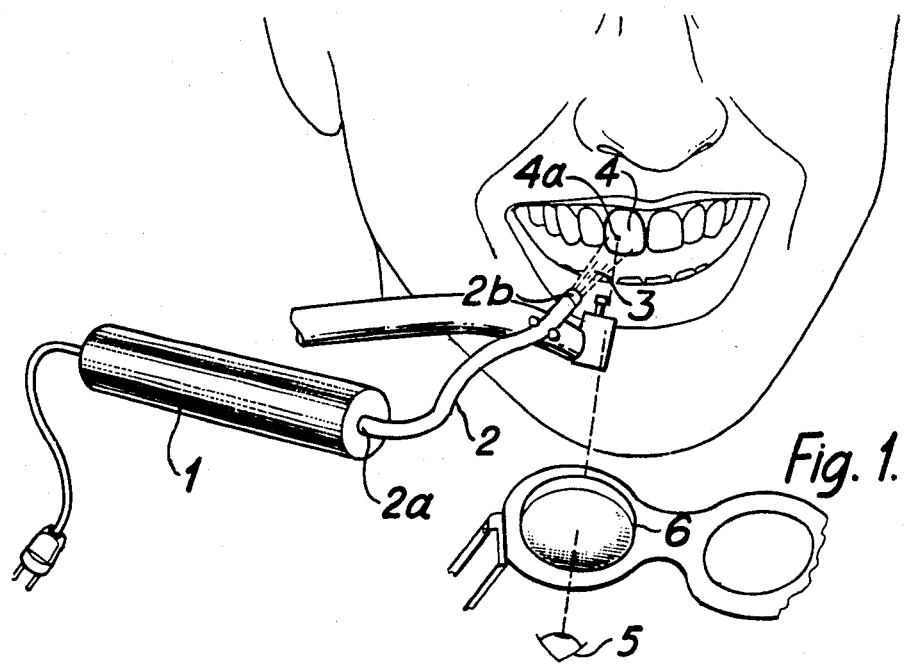
FIG. 1 is a view of a device proposed in accordance with the invention enabling an in vivo determination to be made of any discrepancy in the luminescence capacity of the surface of a tooth.

Before providing a more detailed specification of the proposed device, a brief description will first be made of the fundamental principle of the invention.

The invention relates to the ability to make an instantaneous ocular determination of any discrepancy in the luminescence capacity of the surface of a tooth, and the invention is expected to find a special application whenever there is a need to assess the extent of one or more caried areas on the surface of a tooth.

The principle is based in particular on the illumination of the surface of the tooth by means of a light with a predetermined wavelength, when it has been found that a high proportion of the light will be reflected by the surface of the tooth. It has also been found, however, that the light will cause the activation of the luminescence capacity of the surface of the tooth, when the luminescence emitted by the surface of the tooth may be assumed to lie partly within the spectra of the illuminating light and partly outside the spectra of the light.

The invention is based on the fact that the luminescence capacity of the surface of the tooth is observed under light at a wavelength or within a wave range other than the wavelength or wave range emitted by the device.

By observing the luminescence of the surface of the tooth outside the spectrum of the light intended to be used for illumination, it will be found that the sound surface of a tooth has a high luminescence capacity, but that the luminescence from a caried area is of considerably lower intensity, with any discrepancy in the luminescence capacity of a caried area being seen as a dark area. The surface of the tooth shall preferably be illuminated by a narrow-band light, such as that emitted by a laser, utilizing the natural oscillation of the atoms in order to produce electromagnetic waves within the area of the spectrum between ultraviolet and infrared, including the visible range.

In the event of the surface of the tooth being illuminated by means of a light which is visible to the naked eye, it is proposed in accordance with the invention that the observer shall use an absorption filter capable of absorbing light at the emitted wavelength, when it has been found that the observer will perceive a luminescence at a wavelength which differs slightly from the wavelength of the emitted light, and that a sound tooth will appear light in tone whereas those areas with a different luminescence capacity or with no luminescence capacity due to the presence of caried areas will be perceived by the observer as dark areas.

The invention also proposes the possibility of causing the light to pass through a fibre-optic lead of which the free end may have been treated or designed in such a way as to emit a divergent luminous flux, said luminous flux then being capable of being directed towards one or more surfaces of the tooth.

The invention has also been found to be capable of extending to the ocular determination of any discrepancy in the luminescence capacity of the surface of a tooth produced by the treatment (drilling) of a tooth enabling an assessment to be made during treatment of the extent of a caried area. This requires the surface of the tooth produced by the treatment to be illuminated in the course of the treatment either intermittently or continuously with a light with a predetermined wavelength and/or wave range. It has been found that the luminescence capacity of the surface of the tooth thus formed can be assessed at a wavelength or in a wave range other than that applicable to the light used for illumination, and that the resulting discrepancy between the luminescence capacity of the sound surface of a tooth and that of the caried surface of a tooth may be used in order to determine the extent of the caried area and the point at which the caried part has been removed completely. It has been found that the luminescence from a sound enamel surface and from a sound dentine surface are essentially identical.

With reference to FIG. 1, a detailed specification is now provided of a device for the instantaneous ocular determination of any discrepancy in the luminescence capacity of the surface of a tooth, said device being intended mainly to be capable of assessing the extent of a caried area on the surface of a tooth. The invention utilizes a light-generating device 1, said light-generating device being designed in such a way as to produce a light with a pedetermined wavelength or wave range. The light-generating device 1 may equally consist of a device for producing a narrow-band light, for example a laser device.

The principle of the invention will be explained in greater detail with the help of an argon laser, using a wavelength of 488 nm.

The device 1 could consist of an argon laser of type 171-03 marketed by Spectra Physics of California, USA.

To the device 1 is connected a fibre-optic lead 2 of which one end 2a is connected to the light-generating device 1 and of which the other end 2b will then emit light of the type and at the wavelength generated by the device 1. The luminous beam 3, which in this case is coloured blue and is of an extremely narrow band, is directed at a tooth, shown in the embodiment of the invention as an incisor, of which the buccal surface will then be illuminated by the luminous beam 3. This illumination has now been found to be capable of activating the luminescent capacity of the surface of the tooth, and if the surface of the tooth is sound, then luminescence will occur at a wavelength other than 488 nm. The fundamental idea of invention is to observe the luminescent capacity of the surface of the tooth at a wavelength or within a wave range which is different from the wavelength or wave range of the luminous beam 3, when the sound surface of the tooth will be perceived as being light in colour, although if any part of the surface of the tooth is caried or if any part of the surface of the tooth exhibits a coating or if any part of the surface of the tooth exhibits signs of attack by caries which has already been filled or has defects, then these parts will exhibit a different luminescence capacity or will be entirely lacking in luminescence capacity and these parts will be perceived as dark or black areas.

In the event of the light-generating device 1 consisting of the aforementioned and previously disclosed argon laser, the present invention proposes that an observer 5, in order to be able to make an ocular determination of any discrepancy in the luminescence capacity of the incisor 4, should make use of an absorption filter 6. This filter consists of an absorption filter such that it is capable of absorbing light at a wavelength of 488 nm and should preferably be in the form of laser protective spectacles of type LGS-A marketed by Glendale Inc., USA.

The absorption filter 6 is thus capable only of absorbing light at the wavelength of 488 nm emitted by the device 1, with the result that any areas with a slightly different wavelength will be perceived by the observer. If the argon laser device 1 is used, then a narrow band blue light will be emitted from this at a wavelength of 488 nm, and the sound surface of the tooth will be perceived by the observer 5 wearing absorption spectacles 6 as a bright orange-yellow colour, since light at the wavelength 488 nm will have been absorbed by the filter 6 and the observer 5 will only perceive luminescence at a different wavelength. The caried area will be perceived as black or dark in colour, since such an area will have a very much lower luminescence capacity, and in certain cases none at all, within the range which is visible to the observer.

This means that if the light has a wavelength within the ultraviolet range, then any caried areas should be capable of being assessed without the use of the absorption filter, since the eye is not sensitive to ultraviolet light reflected by the tooth.

Figure 2:
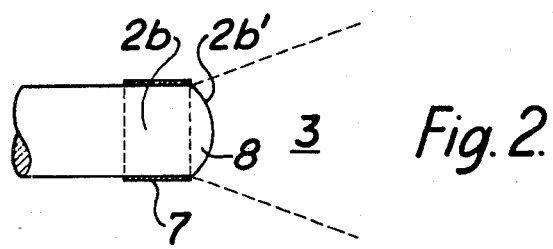
FIG. 2 is a view on an enlarged scale of the front part of a fibre-optic lead utilized in the device in accordance with FIG. 1.

With reference to FIG. 2, an illustration is provided of the free end 2b of the fibre-optic lead 2, from which it can be appreciated that the end surface 2b' has been designed or modified in such a way as to produce a divergent luminous flux 3. It is possible in this way to illuminate the entire surface of the tooth 4 without the need to use a fibre-optic lead 2 of a thickness corresponding to the size of the surface of the tooth. It may be possible to fit the free end 2b with a holder 7 supporting a lens 8 for the purpose of producing a divergent luminous flux covering more than the surface of a single tooth.

Figure 3:
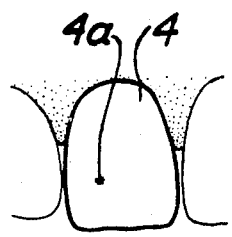
FIG. 3 is a view of the surface of a tooth (an incisor) with an area with incipient caries which is scarcely perceivable by an observer using the method based on the discrepancy in the reflectivity of the surface of the tooth.
Figure 4:
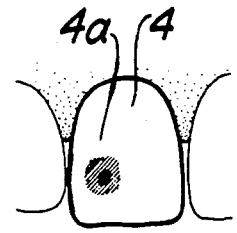
FIG. 4 is a view of the surface of a tooth (an incisor) with the same caried area as in FIG. 3 as it would appear to an observer using the method based on the discrepancy in the luminescence capacity of the surface of the tooth .

With reference to FIG. 3, an illustration is provided of an incisor 4 in which the buccal surface of the tooth exhibits a caried area 4a, and FIG. 3 shows that this area 4a is not perceived by an observer during an examination in which an assessment is to be made of any discrepancy in the reflectivity of the surface of the tooth, since the attack by caries is at an incipient and non-detectable stage, whereas FIG. 4 shows the same buccal surface with the caried area 4a, although in this case an illustration is provided of how this area will appear to an observer during the examination and when the discrepancy in the luminescence capacity of the surface of the tooth is utilized in accordance with the present invention.

Although the present invention generally proposes that the light-generating device 1 shall produce a light with a predetermined wavelength or with a predetermined wave range, it should also be mentioned that particularly high levels of contrast between the various luminescence capacities for the surface of a sound tooth and for a caried area have been obtained with the help of said argon laser at a wavelength of 488 nm and with the help of an absorption filter 6 matched to the same wavelength.

It may be anticipated, however, that the technical effect of the present invention will also be encountered in the case of a light at a shorter wavelength, including the ultraviolet range.

Thus, although the preferred embodiment proposes a fibre-optic lead 2, there is nothing to prevent the light-generating device being designed in such a way that it will emit a luminous flux which is capable of illuminating most of the row of teeth or all the teeth simultaneously.

Although the invention has been described in terms of its ability to assess the extent of caried areas on the surface of a tooth, this shall not be interpreted simply as the external surface of the tooth, but also as those surfaces which may be produced in the course of treatment of the teeth, i.e. enamel surfaces and dentine surfaces.

Thus the device described above may equally be utilized for the ocular determination of any discrepancy in the luminescence capacity of the surface of a tooth produced by the treatment (drilling) of a tooth. It is possible in this way to assess the extent of a caried area in the course of treatment. This may be done by illuminating the surface of the tooth formed by the treatment either intermittently or preferably continuously during treatment by means of a light with a predetermined wavelength and/or wave range. The luminescence capacity of the surface of the tooth thus formed at a different wavelength and/or within an different wave range is assessed in order to be able, on the basis of any discrepancy occurring between the luminescence capacity of the sound surface of a tooth and that of the caried surface of a tooth, to determine the extent of the caried part and the point at which the caried part has been removed completely.

It may be convenient in this case to attach the fibre-optic lead 2 to a tool, for example the drill holder, in such a way that its free end 2b points towards the drilling crown and is able to illuminate the area being subjected to treatment.

The invention is not, of course, restricted to the embodiment indicated above by way of an example, but may undergo modifications within the context of the idea of invention.

I claim:

1. A device for the ocular determination of any discrepancy in the luminescence capacity of the surface of a tooth for assessing the extent of a caried or another defective area of the surface of the tooth, comprising a light generating device for generating light limited at least within a predetermined wavelength range for illuminating the surface of the tooth, and for causing luminescence of the surface of the tooth, the wavelength range of the light being visible to the human eye, an absorption filter for eliminating reflections and luminescence within the wavelength range of the light generating device such that ocular determination of any discrepancy in the luminescence capacity of the tooth surface occurs outside the wavelength range wherein the absorption filter eliminates light only within the wavelength range emitted by the device, whereby every area with a luminescence capacity differing from the luminescence capacity of the surface of a sound tooth will be perceived as a dark area.

2. The device as claimed in claim 1, wherein the light-generating device generates light of a narrow band of wavelengths.

3. The device as claimed in claim 1 or 2, further comprising a fiber-optic lead for transmitting the light emitted by the light-generating device toward the tooth surface.

4. The device as claimed in claim 3, wherein a free end of the fiber-optic lead is treated with an optical substance to produce a divergent luminous flux.

5. The device as claimed in claim 1, wherein the absorption filter is contained in spectacles worn by the observer.

6. The device as claimed in claim 2, wherein the light generating device is a laser.

7. The device of claim 3, wherein a free end of the fiber-optic lead interacts with an optical element to produce a divergent luminous flux.

8. A device for the ocular determination of any discrepancy in the luminescence capacity of the surface of a tooth produced by treatment of a tooth for assessing the extent of a caried area during the treatment, comprising a light source for at least intermittently illuminating the tooth surface produced by the treatment during the course of the treatment, the light source generating light at least within a predetermined wavelength range visible to a human eye, an absorption filter for eliminating reflections and luminescence of the surface of the tooth within the wavelength range such that the surface is directly visually assessed over a different non-modified, reflected wavelength range to permit determination, on the basis of any discrepancy observed between the luminescence capacity of the surface of a sound tooth and the luminescence of the surface of a caried tooth, the extent of the caried area and the extent to which the caried area has been removed.

9. The device as claimed in claim 8, wherein the light source is attached to a tool and is directed towards the area being treated.

10. A device for the ocular determination of any discrepancy in the luminescence capacity of the surface of a tooth for assessing the extent of a caried or another defective area of the surface of the tooth, comprising a light generating device for generating light limited at least within a predetermined wavelength range for illuminating the surface of the tooth, and for causing luminescence of the surface of the tooth, the wavelength range of the light being visible to the human eye, an absorption filter for eliminating reflections and luminescence within the wavelength range of the light generating device such that ocular determination of any discrepancy in the luminescence capacity of the tooth surface occurs outside the wavelength range wherein the absorption filter eliminates light within the wavelength range emitted by the device, whereby every area with a luminescence capacity differing from the luminescence capacity of the surface of a sound tooth will be perceived as a dark area.

* * * * *

UNITED STATES PATENT AND TRADEMARK OFFICE
CERTIFICATE OF CORRECTION

PATENT NO. : 4,515,476
DATED      : May 7, 1985
INVENTOR(S): Hans I. Bjelkhagen

It is certified that error appears in the above-identified patent and that said Letters Patent is hereby corrected as shown below:   On the title page:

Change the order of the names of Applicant to read

-- HANS I. BJELKHAGEN --.

Signed and Sealed this

Twenty-seventh Day of August 1985

[SEAL]

Attest:

DONALD J. QUIGG

Attesting Officer    Acting Commissioner of Patents and Trademarks